US00PP22239P2

(12) United States Plant Patent
Madsen

(10) Patent No.: US PP22,239 P2
(45) Date of Patent: Nov. 8, 2011

(54) ***SCHLUMBERGERA* PLANT NAMED 'PKMSC01'**

(50) Latin Name: *Schlumbergera truncata*
Varietal Denomination: PKMSC01

(75) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 0 days.

(21) Appl. No.: 12/800,564

(22) Filed: May 18, 2010

(51) Int. Cl.
*A01H 5/00* (2006.01)

(52) U.S. Cl. ..... Plt./372

(58) Field of Classification Search ..... Plt./372
See application file for complete search history.

(56) References Cited

OTHER PUBLICATIONS

Upov Plant Variety Database 2011/ 02 Search for PKMSC01 cultivar.*
Print-out of application number and filing data from Community Plant Variety Office (CPVO) website for corresponding, CPVO application No. 2008/2927 filed Dec. 17, 2008 (3 pages). (http://www.cpvoextranet.cpvo.europa.eu).

* cited by examiner

*Primary Examiner* — Annette Para
(74) *Attorney, Agent, or Firm* — Foley & Lardner

(57) ABSTRACT

A new and distinct *Schlumbergera truncata* plant named 'PKMSC01' particularly characterized by large upright to vertical flowers; flowers which have petals which are red-purple (RHS 68A) and a white throat (RHS NN155D); large quantity of flowers per plant; slow growth habit and freely branching habit; and ovoid to lanceolatoid buds, which are yellow-green (RHS 145D) in color.

8 Drawing Sheets

Latin name of the genus and species of the plant claimed: *Schlumbergera truncata.*

Variety denomination: 'PKMSC01'.

BACKGROUND OF THE INVENTION

The present invention relates to a new and distinct cultivar of *Schlumbergera* plant, botanically known as *Schlumbergera truncate* (Haworth) Moran., commonly known as Christmas Cactus, and hereinafter referred to by the cultivar name 'PKMSC01'.

*Schlumbergera* (formerly *Zygocacatus*) of the Cactaceae family, consists of 6 known species which are epiphytic cacti and native to Brazil. Common names for *Schlumbergera* plants include: Crab Cactus for the cultivar's claw-like phylloclade margin, Thanksgiving Cactus for cultivars which bloom in November, and Christmas Cactus for cultivars which bloom in December.

The new *Schlumbergera* 'PKMSC01' is a product of a controlled breeding program conducted by the inventor, Christian Hald Madsen, in Søhus, Denmark. The objective of the breeding program was to develop a new *Schlumbergera* cultivar with an upright and compact plant habit and flowers with a unique color combination.

The new *Schlumbergera* 'PKMSC01' originated from a cross made by the inventor, Christian Hald Madsen, in 2002 in Søhus, Denmark, between two unnamed, unpatented proprietary *Schlumbergera truncate* (Haworth) Moran. cultivars. The new *Schlumbergera* 'PKMSC01' was discovered and selected by the inventor as a single flowering plant within the progeny of the stated cross in a controlled environment in 2006 in Søhus, Denmark. The inventor selected the new *Schlumbergera* 'PKMSC01' based on its compact, freely branching habit and unique flower color.

Asexual reproduction of the new *Schlumbergera* 'PKMSC01' by phylloclade cuttings, followed by trial production batches, was first performed in April of 2007 in Søhus, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'PKMSC01' which in combination distinguish this *Schlumbergera* as a new and distinct cultivar:

1. Large upright to vertical flowers;
2. Flowers which have petals which are red-purple (RHS 68A) and a white throat (RHS NN155D);
3. Large quantity of flowers per plant;
4. Slow growth habit and freely branching habit; and
5. Ovoid to lanceolatoid buds, which are yellow-green (RHS 145D) in color.

No plants of either parent, both an unnamed, unpatented proprietary *Schlumbergera truncate* (Haworth) Moran. line, are available to provide a botanical comparison to the new *Schlumbergera* 'PKMSC01'.

Of the many commercial cultivars known to the present inventor, the most similar in comparison to the new *Schlumbergera* 'PKMSC01' is the unpatented *Schlumbergera truncate* (Haworth) Moran. 'Dark Eva'. In side-by-side comparisons trials conducted over several seasons by the inventor in Søhus, Denmark, plants of 'PKMSC01' differ from plants of 'Dark Eva' in the following characteristics:

1. Plants of 'PKMSC01' produce wider phyllocladia (measuring about 30 to 40 mm width) than plants of 'Dark Eva' (phyllocladia measuring about 20 to 30 mm);
2. Plants of 'PKMSC01' produce yellow-green (RHS 145D) buds whereas plants of 'Dark Eva' produce red-purple (RHS N67B) buds;
3. Plants of 'PKMSC01' produce a striking mature flower color combination of red-purple (RHS 68A) petals with a white (RHS NN155D) throat, whereas plants of 'Dark Eva' produce flowers with a mature flower color combination of red-purple (RHS N74A) petals with a white (RHS NN155D) throat; and
4. Plants of 'PKMSC01' produce yellow-green sepals (RHS 145C) whereas plants of 'Dark Eva' produce greyed-purple sepals (RHS 187D).

BRIEF DESCRIPTION OF THE PHOTOGRAPHS

The accompanying photographs illustrate the overall appearance of the new *Schlumbergera* cultivar 'PKMSC01' showing the colors as true as is reasonably possible with colored reproductions of this type. Colors in the photographs may differ slightly from the color values cited in the detailed botanical description, which accurately describe the color of 'PKMSC01'.

DETAILED BOTANICAL DESCRIPTION

Figure 1:
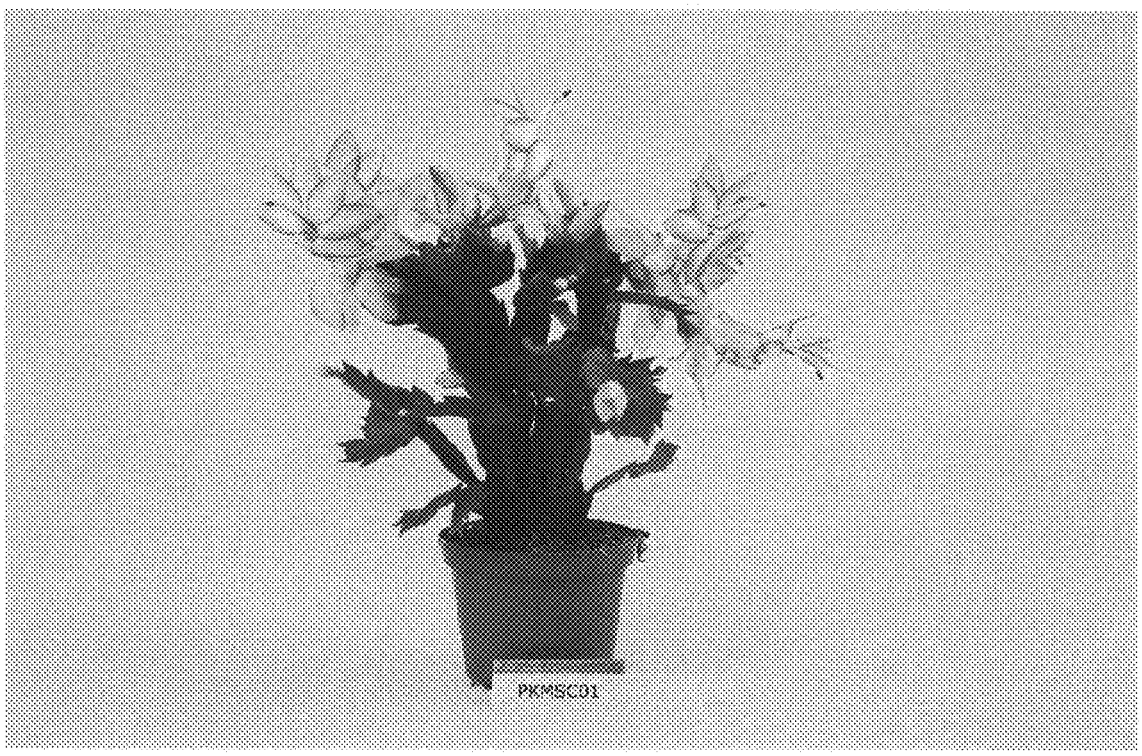
FIG. 1 shows a side perspective view of a typical flowering plant of 'PKMSC01', grown in a 9 cm pot, about 24 weeks after planting of rooted cutting.
Figure 2:
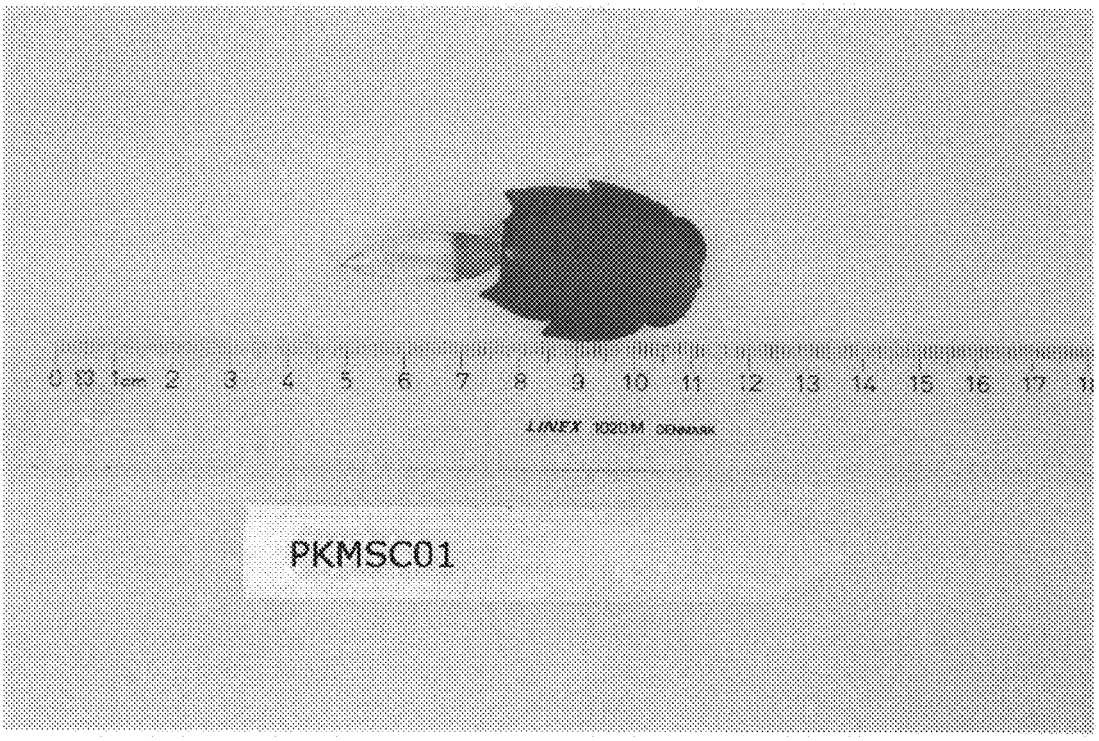
FIGS. 2 shows a close-up view of a typical bud of 'PKMSC01'
Figure 3:
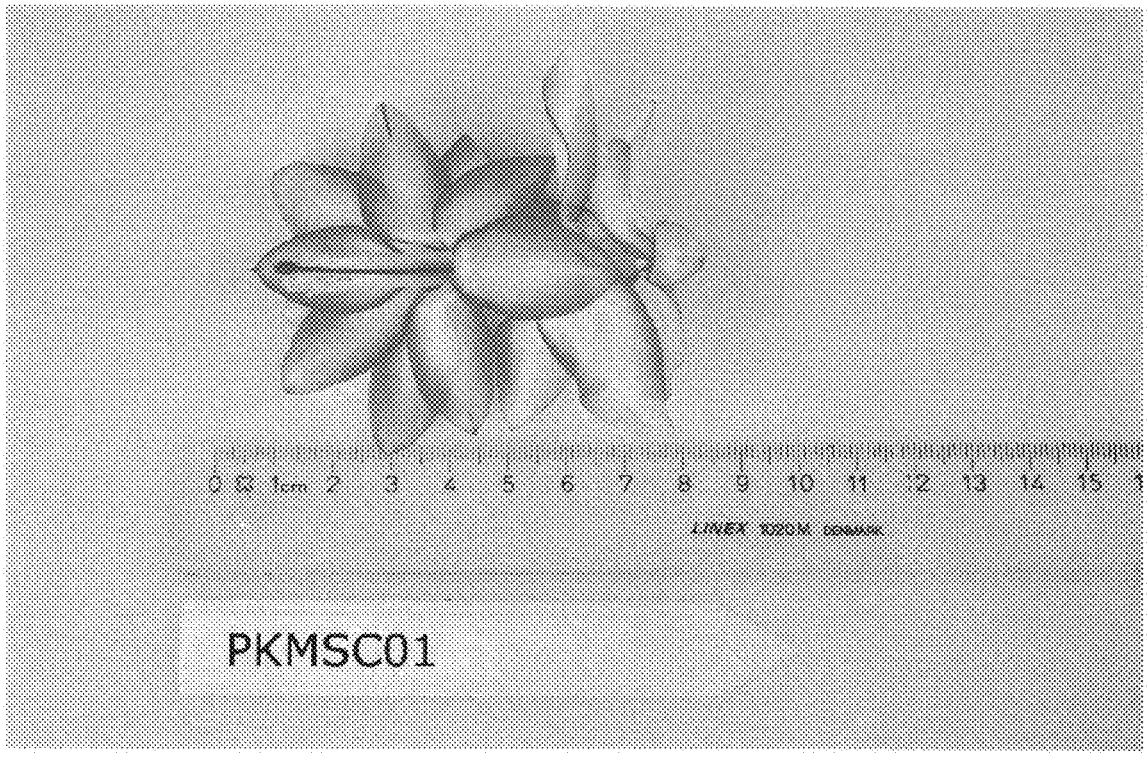
FIG. 3 shows a close-up view of a typical flower of 'PKMSC01'
Figure 4:
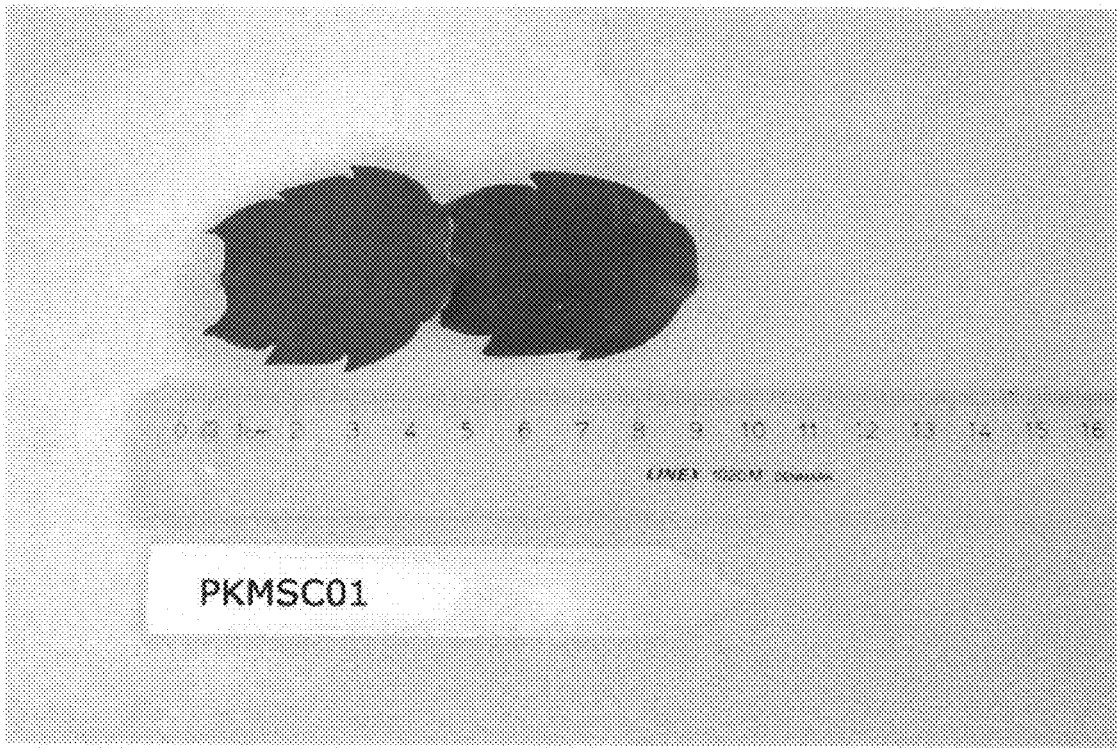
FIG. 4 shows a close-up view of typical phyllocladia of 'PKMSC01'
Figure 5:
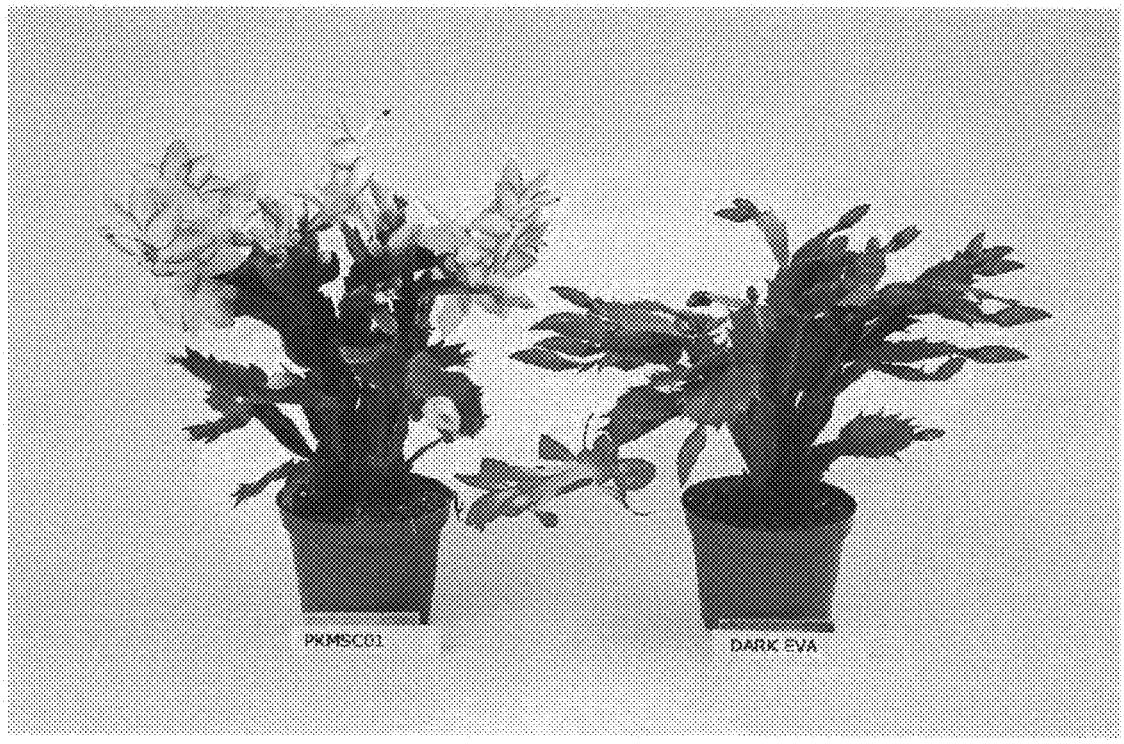
FIG. 5 shows side-view comparison view of a typical flowering plant of 'PKMSC01' (on the left) and a typical flowering plant of the comparison cultivar 'Dark Eva' (on the right).
Figure 6:
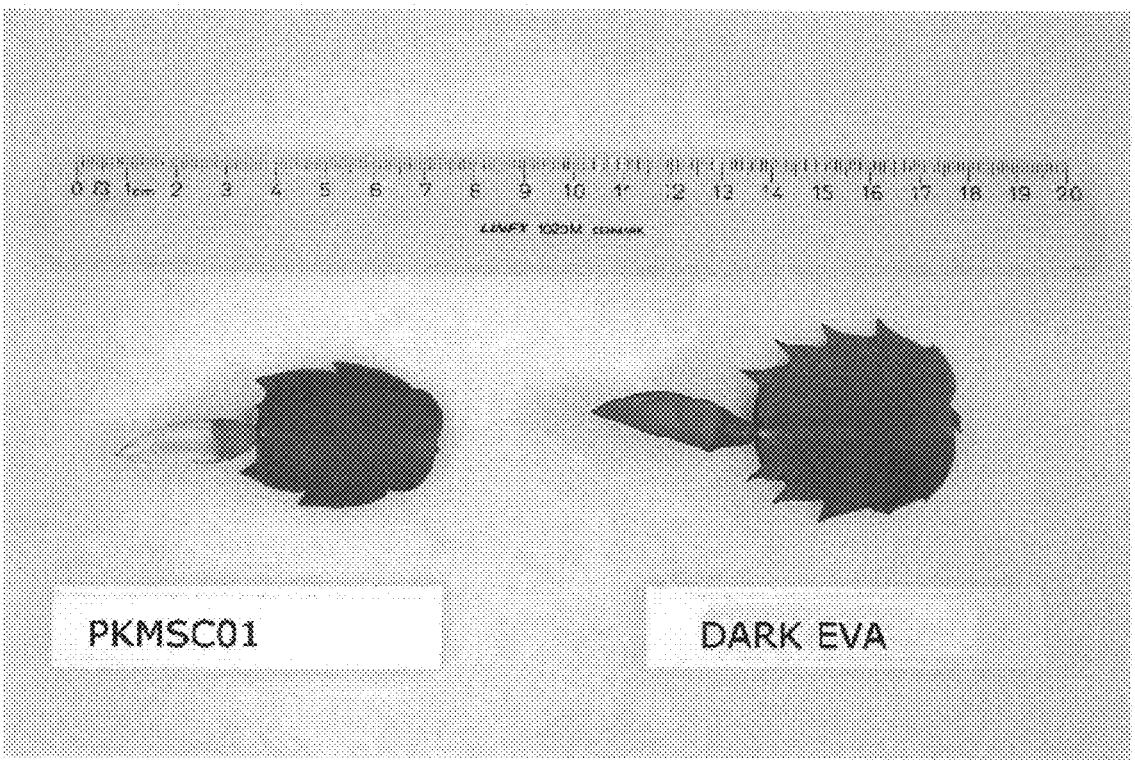
FIG. 6 shows a side-view perspective view of a typical bud of 'PKMSC01' compared to a typical bud of the comparison cultivar 'Dark Eva'.
Figure 7:
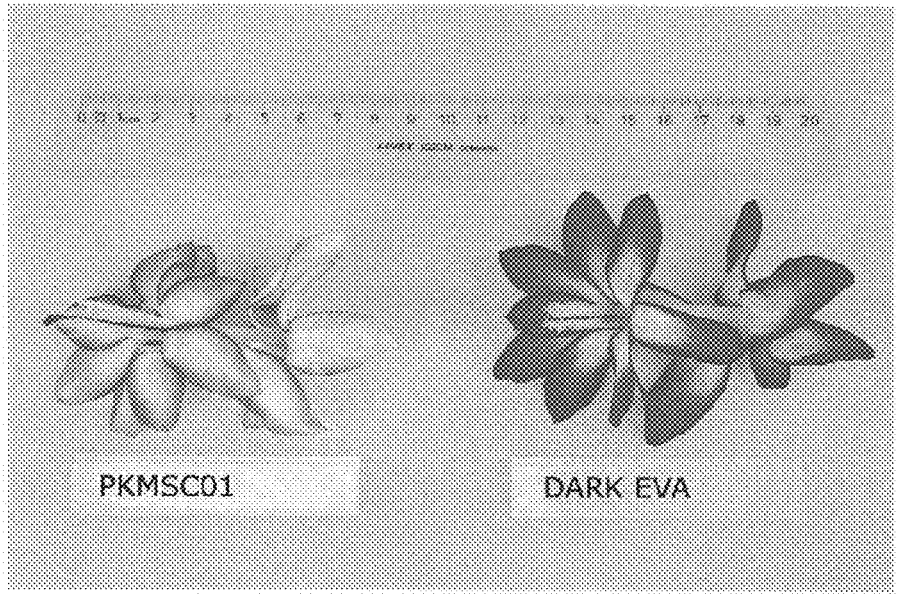
FIG. 7 shows a side-view perspective view of a typical fully-opened flower of 'PKMSC01'compared to a typical fully-opened flower of the comparison cultivar 'Dark Eva'.
Figure 8:
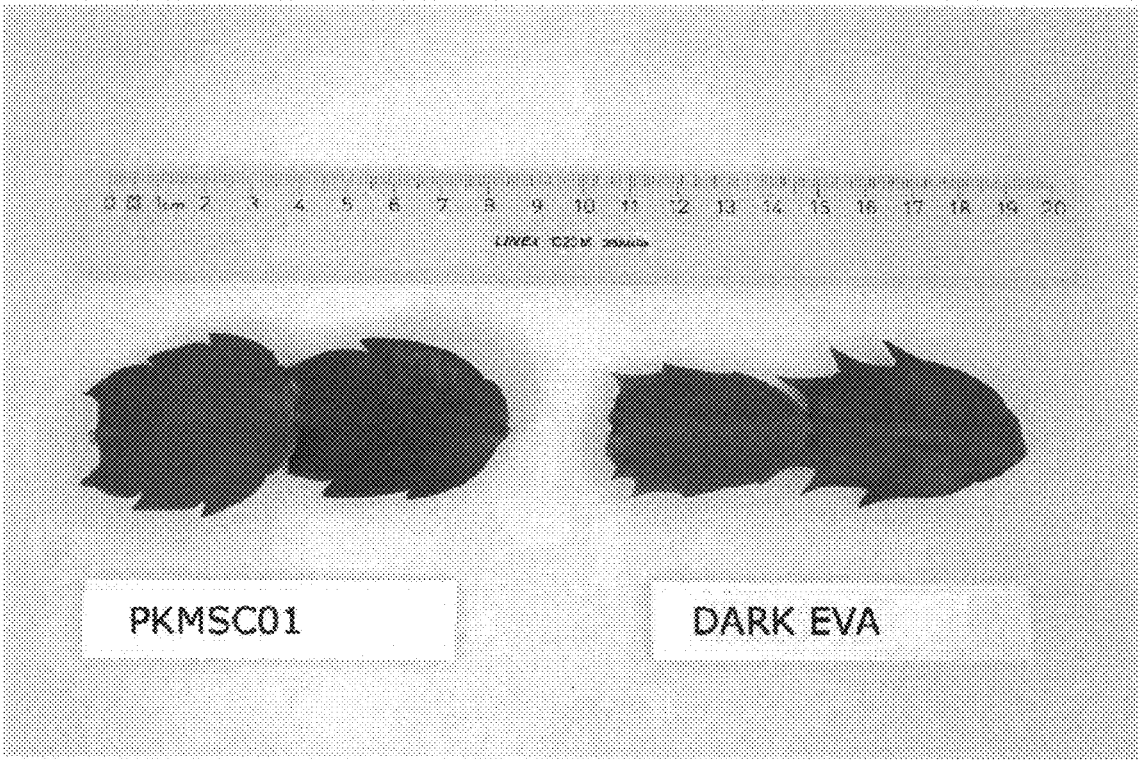
FIG. 8 shows a side-view perspective view of typical phyllocladia of 'PKMSC01' compared to a typical phyllocladia of the comparison cultivar 'Dark Eva'.

The new *Schlumbergera* 'PKMSC01' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'PKMSC01' as grown in a glass-covered greenhouse in Fyn, Denmark, under conditions which closely approximate those generally used in commercial practice. Plants of 'PKMSC01' are themo-photo-periodic and will develop buds and bloom best under short day conditions (less than 12 hours of sunlight for a period of 6 weeks) and cool night temperatures between 15° C. and 18° C. Plants of 'PKMSC01' are grown under an average day temperate of 18° C. and an average night temperature of 18° C. Ambient light levels of +120W m2 were used and no growth retardants were applied when growing plants of 'PKMSC01'.

Color references are made to The Royal Horticultural Society Colour Chart (R.H.S.), 4$^{th}$ edition, except where general colors of ordinary significance are used. The photographs and descriptions were taken during the winter season of 2009 in Fyn, Denmark, when outdoor day temperatures averaged 5° C. and outdoor night temperatures averaged 0° C. The age of the plants described is about 24 weeks after rooting of cutting.

Classification:

*Botanical.*—*Schlumbergera truncata.*

*Common name.*—Christmas Cactus.

Parentage:

*Female or seed parent.*—Unnamed, unpatented proprietary *Schlumbergera truncate* (Haworth) Moran. cultivar.

*Male or pollen parent.*—Unnamed, unpatented proprietary *Schlumbergera truncate* (Haworth) Moran. cultivar.

Propagation: By single, mature phylloclade cuttings.

*Time and temperature to initiate roots.*—In a greenhouse, about 16 days at 21° C.

*Time and temperature to produce a rooted cutting.*—In a greenhouse, about 16 days at at 21° C.

*Rooting habit and description.*—Fine, fibrous and well-branched.

Plant:

*Type.*—Perennial, Epiphyte.

*Growth habit.*—Young plants have erect and upright habit. Mature plants become slightly pendent as lateral branches lengthen.

*Branching habit.*—Freely branching, with two or three phyllocladia forming at the apical ends of older phyllocladia. Single or double (seldom triple) sessile flowers borne on apical end of phylloclade.

*Vigor.*—Slow growth rate.

*Crop time.*—After rooting of mature phylloclade cutting, about 24 weeks are required to produce a finished flowering plant in an 9 cm pot.

*Size at maturity.*—Height (soil level to top of plant, including flowers): About 15 cm. Spread: About 24 cm to 25 cm.

Stem: None, older phyllocladia may turn woody with age (several years).

Lateral branches:

*Arrangement.*—Phyllocladia form at the apical end of older phyllocladia to form branches.

*Branching habit.*—Freely.

*Basal branching.*—Yes.

*Quantity.*—About 6 to 12.

*Length.*—Primary: About 10 cm (3-4 phylloclade). Secondary: About 4 cm to 5 cm (1-2 phyllocladia).

*Width.*—About 3 cm to 4 cm.

*Aspect.*—Upright (from basal phylloclade).

*Strength.*—Strong (from basal phylloclade).

*Appearance.*—Glabrous, smooth.

*Pubescence.*—None.

*Color.*—Green, RHS 137A.

Phylloclade:

*Arrangement.*—Single and sequential.

*Quantity per lateral branch.*—About 3 to 4.

*Length.*—About 3 cm to 4 cm.

*Width.*—About 3 cm to 4 cm.

*Thickness.*—About 4 mm (center of phylloclade).

*Overall shape.*—Oval.

*Apex shape.*—Truncate with 2 protruding marginal teeth (about 5 mm to 6 mm in length), forming a claw-like shape.

*Base shape.*—Rounded.

*Margin.*—Serrated; about 2 to 4 teeth (about 6 mm to 7 mm in length).

*Texture.*—Glabrous, smooth.

*Pubescence.*—None.

*Color* (*mature*).—Upper surface: Green, RHS 137C; Under surface: Green, RHS 137C; Margin: Green, RHS 137C.

*Color* (*immature*).—Upper surface: Green, RHS 137A; Under surface: Green, RHS 137A; Margin: Green, RHS 137C.

*Venation.*—Pattern: Costate. Color: Upper surface: Green, RHS 137A; Lower surface: Green, RHS 137A.

Areole: Not true areole structure; tip of phylloclade is barbellulate with about 10 to 15 stiff hairs.

Inflorescence description:

*Arrangement and appearance.*—Single or double (seldom triple) sessile flowers borne on apical end of phyllocladia. Flowers are hose-in-hose, tubular and zygomorphic. When flowers are fully open, they form a right angle to the phylloclade. Flowers persistent; petals fold and wither slowly.

*Natural flowering season.*—Flowering occurs from October to January (Northern hemisphere), but can be changed depending on short day photo-treatments.

*Flowering response time.*—About 8 to 9 weeks from planting.

*Rate of flowers opening.*—About 1 to 2 per week, depending on temperature and light.

*Flowering longevity* (*dependent on temperature and light conditions*).—About 5 to 6 days.

*Fragrance.*—None.

*Quantity of flowers per lateral branch.*—About 1 to 3.

*Quantity of buds per lateral branch.*—About 2.

*Quantity of flowers and buds per plant.*—About 25 to 30.

*Flower bud.*—Length: Ranging from 0 to 3.5 cm (before anthesis). Width: Ranging up to 1 cm (before anthesis). Shape: Ovoid to lanceolate. Color: Yellow-green, RHS 145D.

*Flower.*—Type: Single. Shape: Tubular, hose-in-hose triple perianth. Aspect: Initially upright, later facing outward (right angle to phylloclade). Persistent or self-cleaning: Persistent, but drops after withering.

*Corolla size.*—Depth: About 7 cm (including ovary). Diameter: About 5 cm to 6 cm. Tube length: About 4 cm. Tube diameter: About 8 mm.

*Petals.*—Quantity: Apical Whorl: About 5 to 7; Basal whorl: About 10. Length: About 2.6 cm to 4.2 cm. Width: About 1.5 cm to 2.0 cm. Shape: Oval. Apex: Retuse. Base: Apical Whorl: Fused; Basal Whorl: Free. Margin: Entire. Appearance: Smooth. Texture: Silky (both surfaces). Color of Upper Surface (when opening and when fully opened): Lobe: Red-purple, RHS 68A; Tube: White, RHS NN155D. Color of Under Surface (when opening and when fully opened): Lobe: Red-purple, RHS 68A; Tube: White, RHS NN155D. Color Fades to: Lobe: Red-purple, RHS 68A; Tube: Orange-yellow, RHS 19C.

*Petaloids.*—None.

*Calyx.*—Shape: Tube. Length: Up to 10 mm. Diameter: Up to 5 mm.

*Sepals.*—Appearance: Bud-like. Arrangement: Free. Quantity: About 4. Length: Up to 10 mm. Width: Up to 8 mm. Shape: Ovate. Apex: Obtuse to rounded. Base: Truncate. Margin: Entire. Texture (both surfaces): Silky. Color (Immature and Mature): Upper and Under Surfaces: Yellow-green, RHS 145C.

Reproductive organs:

*Androecium.*—Stamen: Quantity: Many (about 50 to 70), polyandrous, incurved. Some filaments fused to perianth tube (connate); about 5 mm from receptacle. Length: About 50 mm. Color: Translucent, white, RHS 155D. Anther: Shape: Basifixed, ovoid. Length: About 1 mm. Color: Yellow-orange, RHS 17A. Filament: Length: About 40 mm to 45 mm. Color: Translucent, white, RHS 155D. Pollen: Amount: Abundant. Color: Yellow-orange, RHS 17A.

*Gynoecium.*—Pistil: Quantity: 1. Shape: Slightly curved. Length: About 60 mm. Stigma: Shape: Claw-like. Color: Red-purple, RHS 78A, with RHS 77A at tip. Style: Length: About 45 mm. Color: White, RHS 155D. Ovary: Shape: Angular. Length: About 4 mm to 5 mm. Width: About 3 mm. Color: Yellow-green, RHS 149D.

Seeds/fruit: None observed.

Disease/pest resistance: No test for disease/pest resistance have been performed yet.

Disease/pest susceptibility: No test for disease/pest resistance have been performed yet.

Temperature tolerance: Tolerant to a low temperature of about +2° C. and to a high temperature about +40° C.

Drought tolerance: Good.

What is claimed is:

1. A new and distinct *Schlumbergera truncata* plant named 'PKMSC01', as illustrated and described herein.

* * * * *